United States Patent

Kabanek

[11] Patent Number: 5,921,407
[45] Date of Patent: Jul. 13, 1999

[54] HOLDER FOR HOLDING SURGICAL INSTRUMENTALITIES IN SPREAD ARRANGEMENT

[76] Inventor: Sandra S. Kabanek, 32390 IH-10 West, Boerne, Tex. 78006

[21] Appl. No.: 08/883,651

[22] Filed: Jun. 27, 1997

[51] Int. Cl.⁶ ............................................. A47B 81/02
[52] U.S. Cl. ...................... 211/65; 211/88.01; 211/85.13
[58] Field of Search ............................. 211/65, 66, 85.13, 211/88.01, 13.01; 248/205.5

[56] References Cited

U.S. PATENT DOCUMENTS

| | | | |
|---|---|---|---|
| 507,233 | 10/1893 | Marshall | 211/88.01 X |
| 776,332 | 11/1904 | Kloeppinger | 211/88.01 X |
| 843,826 | 2/1907 | Kloeppinger | 211/88.01 X |
| 1,552,510 | 9/1925 | Scofield | 211/88.01 |
| 1,955,736 | 4/1934 | Claytor et al. | 211/88.01 X |
| 2,269,940 | 1/1942 | Johnson | 211/65 X |
| 2,627,982 | 2/1953 | Williams | 211/88.01 |
| 2,733,113 | 1/1956 | Humbargar | 211/88.01 X |
| 2,771,219 | 11/1956 | Dewey | 248/205.5 X |
| 4,326,761 | 4/1982 | Schwartz | 211/88.01 X |
| 4,415,089 | 11/1983 | Ruffa | 211/85.13 |
| 4,607,752 | 8/1986 | Sherrow | 211/65 |
| 5,624,091 | 4/1997 | Protz, Jr. | 248/205.5 |
| 5,630,517 | 5/1997 | Maznik | 248/205.5 X |

*Primary Examiner*—Blair M. Johnson
*Attorney, Agent, or Firm*—Paul H. Gallagher

[57] ABSTRACT

A brush holder having a back panel for holding the brushes in spread position, and a trough in front at the bottom for holding related items. The entire back panel and trough are integral, and made of steel. Support hooks with transparent suction cups are mounted on the back panel.

1 Claim, 2 Drawing Sheets

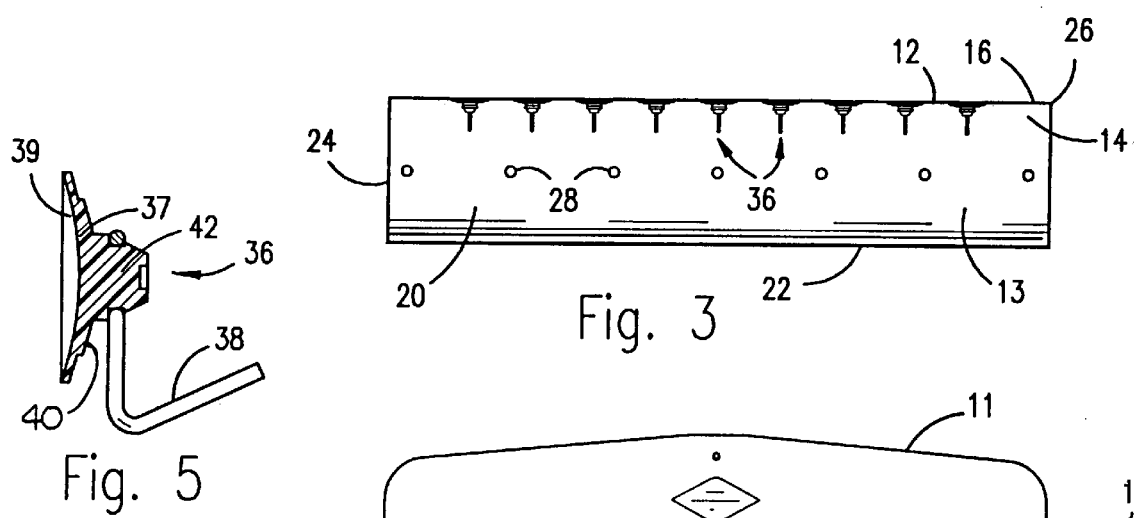
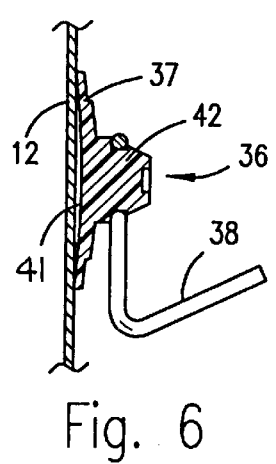
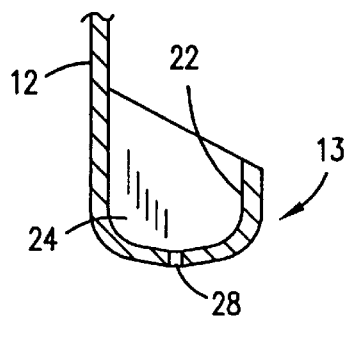
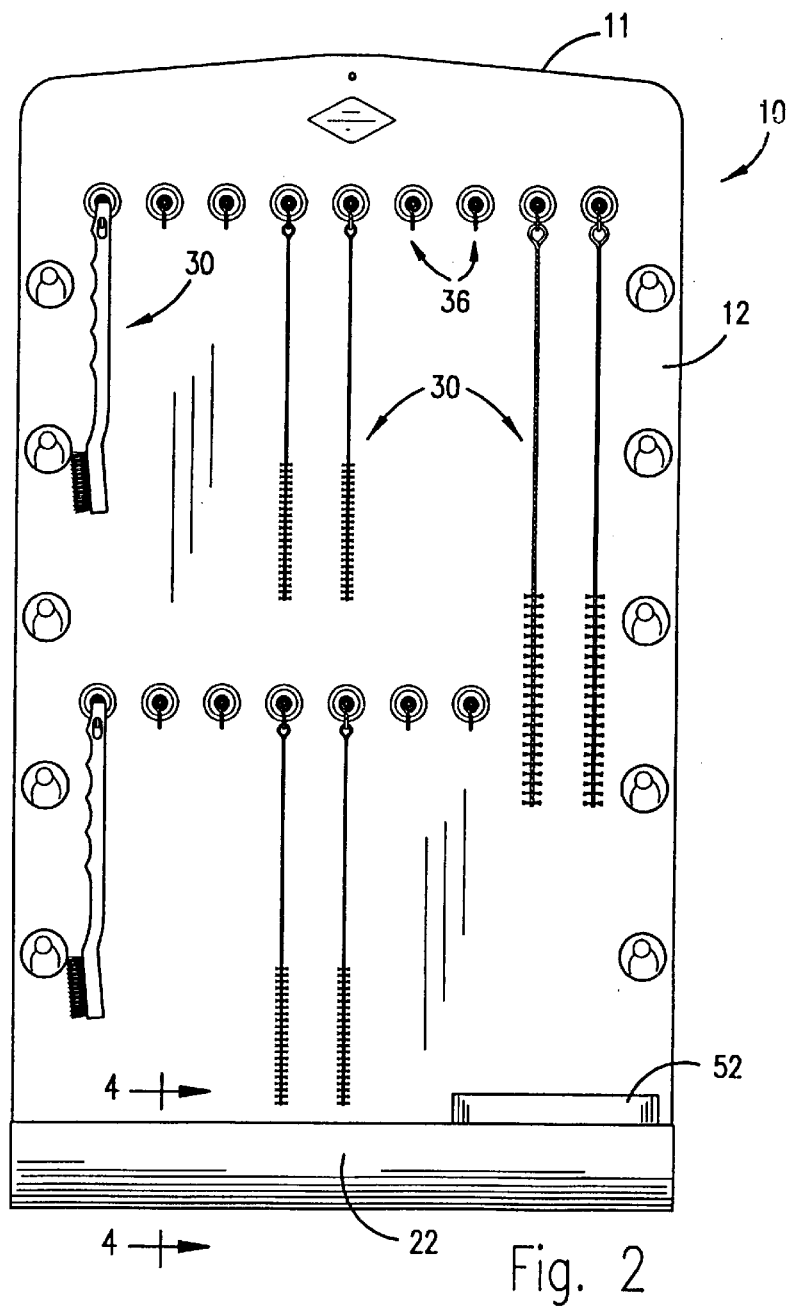

HOLDER FOR HOLDING SURGICAL INSTRUMENTALITIES IN SPREAD ARRANGEMENT

SUMMARY OF THE INVENTION

The device of the invention is for use in the medical field, and particularly in connection with the surgical phases thereof. Essentially, it is a device for holding instrumentalities that are used in that field, such as cleaning brushes and similar items. Such items are to be used particularly in connection with cleansing and disinfecting surgical instruments, and related items, and in such steps, a number of different kinds of brushes are used, and they are generally used in connection with a particular series of steps, such that one brush may be used and shortly thereafter another brush, and during this series of steps, the articles being cleansed must be held, so that generally only one hand is free to pick up brushes and replace them. Directly connected with this step is the fact that brushes in between steps of use must be put in a place where they do not touch other objects, so as to be maintained in clean condition.

Brushes used in this phase of the operation usually are elongated, with a long handle, and a brush element at one end that is relatively short. It is the brush elements themselves that must be protected, that is, not be contaminated by touching other articles.

The device of the present invention includes as a large part, a panel on which the brushes may be hooked and suspended, with the brush elements, or working ends, held generally in suspended position without touching other articles, except the body of this device itself, and thus maintaining them in clean condition for continuing use.

A more particular object is the provision of such a device which has a large area for accommodating the brushes to be hung and supported in spread condition, so that they can be easily picked out and replaced, and when suspended on the panel do not touch other articles, at least to any great extent.

Another object is to provide such a device, having hooks for holding the brushes and related items, that is of very pleasant appearance, the hooks being relatively inconspicuous.

Still another object is to provide such a device that is of very simple construction and thereby relatively easily maintained in clean condition.

Still another object is to provide a device of the foregoing character, which includes a main large panel for supporting the brushes and related items, and which has an unusually simple construction affording also a pocket at the lower end for holding other related items.

BRIEF DESCRIPTIONS OF INDIVIDUAL FIGURES OF THE DRAWINGS

FIG. 2 is a front view.

FIG. 3 is a top view.

FIG. 4 is a fragmentary sectional view taken at line 4—4 of FIG. 2.

FIG. 5 is a sectional view of a hook, and suction cup, for holding the brushes.

FIG. 6 is a sectional view of the suction cup of FIG. 5 as applied to the panel of the holder.

DETAILED DESCRIPTION OF THE DRAWINGS

Figures 1, 7, 8:
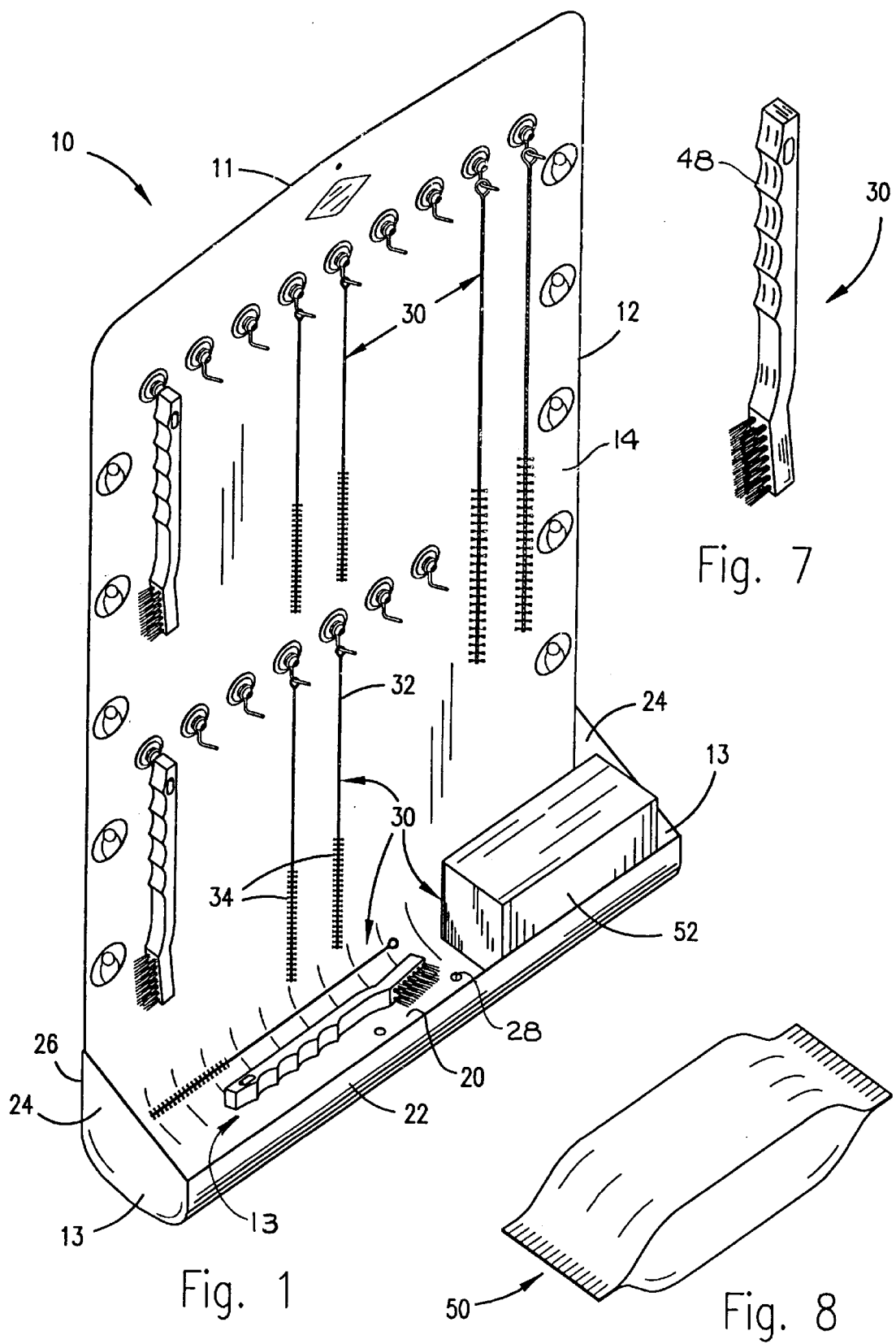
FIG. 1 is a perspective view of the device embodying the present invention.
FIG. 7 is a view of another item that may be hung on a hook, or accommodated in the trough of the device.
FIG. 8 is a view of another article that may be held in the trough of the holder.

The holder of the invention is indicated at 10 and shown in perspective view in FIG. 1. It includes a main member 11 having a back panel 12 and a front trough 13, the back panel being vertically disposed in the usable position of the device. The back panel is relatively large for enabling a large number of brushes or items to be mounted thereon in spread form, and while these dimensions are not limited, a practical size of the device may be in the neighborhood of 30" high and 18" wide.

For convenience in the following description, the holder is considered as oriented in FIGS. 1 and 2, and thus vertically disposed as indicated above, and as so oriented has a front side 14 presented to the observer, and an opposite back side 16.

The panel 12 is preferably a straight, flat member, and at the bottom is bent forwardly and upwardly to form the trough 13, having a bottom element 20, and a front element 22 extending substantially vertically. This trough may be of suitable dimensions, such as 3–4" in front to back dimension, and in the neighborhood of 3" deep.

The trough is completed by end pieces 24 preferably inclined downwardly in forward direction, their upper edges coinciding with the upper edge of the front element 22.

The elements making up the main member are integral, and preferably steel or iron. The end pieces 24 are integral continuations of the body of the back panel 12, bent at 26 and are welded or soldered to the bottom part and front part of the trough. The integral formation simplifies manufacturing and reduces seams and correspondingly facilitates sanitation. The use of steel also enables magnetic elements to be releasably held thereon. As used herein, steel includes iron and welding includes soldering. the bottom element 20 is provided with drain holes 28.

Various brushes and similar items 30 are mounted on the main panel. These brushes are generally of the type having a long handle 32 and a brush element 34 at one end. A number of this kind of brushes are usually required and for mounting them on the panel, support hooks 36 are provided. These support hooks are shown in detail in FIGS. 5 and 6, and each includes a suction cup 37 and a steel hook 38. The suction cup is of transparent plastic, and has a concave inner surface 39 and a convex outer surface 40. It is flexible to a position wherein the inner surface flattens (FIG. 5) and nearly, but not entirely, engages the back panel, as shown in FIG. 6. A very slight space is indicated at 41. On the outer convex side is a button 42 on which the steel hook 38 is detachably snapped, the hook being then swingable thereon. The suction cup is thus held firmly on the panel and is very inconspicuous, and since it is transparent, the entire support hook is many times unnoticeable.

These support hooks may be applied in such number and at such locations as to accommodate the number of brushes and related items that are to used.

Many of the brushes used are relatively long, and the panel of the holder is of such dimensions as to accommodate extremely long brushes without the lower ends entering into the trough, to any substantial extent, thus maintaining the brushes that are so hung, away from other articles, and thus correspondingly isolated. The panel is also of such width as to enable the support hooks to be spaced apart a substantial distance, even when a large number of them are used, as to facilitate grasping the brushes by the hand.

The brushes of the kind shown here hung on the panel, constitute the greater number of kind of brushes that are usually to be accommodated, but other items are also required and used, such as a single hand brush 48 of FIG. 7, and a package 50 or 52 (FIGS. 1, 8), which may be another shape of brush, or other article, enclosed in a wrapper.

The holder itself, with the brushes to be utilized, may be assembled in a set, and sold as such a set, or kit. Also the complete set may be displayed in set-up condition for observation by prospective customers.

I claim:

1. A device for holding brushes in spread position, and related articles, comprising, a main member made of steel including a back panel, and adapted for placing in a usable position with the back panel in vertical position, the main member having a front side and a back side, the main member also including a trough on the front side of and at the lower end of the back panel, the trough including a body element integral with the back panel extending the full width of the back panel and forming a continuation of the back panel, and turned upwardly at the front, and end pieces at the ends of the space in the trough integral with the back panel and bent perpendicular to the back panel and welded to the end edges of the body element of the trough throughout the extent of the trough in planes perpendicular to the back panel, the upper edges of the end pieces being inclined downwardly in forward direction, with their front ends coincident with the upper edge of the front side of the trough, the front side of the back panel forming a plane surface extending the full height of the back panel from the top of the device down to the trough, the trough having drain holes therein, and the device including support hooks mounted on the back panel on the front side of the latter and distributed throughout a substantial portion of the area of the back panel for hanging instruments thereon over the trough, each support hook including a suction cup of transparent plastic material, each suction cup including a cup element having a concave side, and when applied to the back panel with the concave side engaged with the panel, is so flexible as to enable the suction cup to flex, and thereby to cause the concave surface to flatten and nearly, but not entirely, engage the surface of the back panel, the suction cup having a front convex side and a button extending from the front side, and the support hook also including a metal hook element detachably and swingably mounted on the button, the entire device, except for said support hooks being made up entirely of the main member.

\* \* \* \* \*